United States Patent
Serra Autonell

(10) Patent No.: US 8,233,970 B2
(45) Date of Patent: Jul. 31, 2012

(54) METHOD FOR PROCESSING CARDIOELECTRIC SIGNALS AND CORRESPONDING DEVICE

(75) Inventor: Guillem Serra Autonell, Taradell (ES)

(73) Assignee: GEM-MED S.L., Barcelona (ES)

( * ) Notice: Subject to any disclaimer, the term of this patent is extended or adjusted under 35 U.S.C. 154(b) by 763 days.

(21) Appl. No.: 12/374,418

(22) PCT Filed: Jul. 19, 2007

(86) PCT No.: PCT/EP2007/006418
§ 371 (c)(1),
(2), (4) Date: Jan. 20, 2009

(87) PCT Pub. No.: WO2008/014895
PCT Pub. Date: Feb. 7, 2008

(65) Prior Publication Data
US 2010/0016747 A1    Jan. 21, 2010

(30) Foreign Application Priority Data
Aug. 4, 2006 (ES) .................................. 200602123

(51) Int. Cl.
*A61B 5/0452* (2006.01)
(52) U.S. Cl. .......... 600/509; 600/510; 600/512; 600/516
(58) Field of Classification Search .................. 600/509, 600/510, 512, 513, 516, 517
See application file for complete search history.

(56) References Cited

U.S. PATENT DOCUMENTS
5,782,888 A    7/1998  Sun et al.
6,438,196 B1   8/2002  Cesmeli
2004/0193065 A1 9/2004 Houben FOREIGN PATENT DOCUMENTS
WO  WO 02/058550 A2   8/2002
WO  WO 2006/081447 A2 8/2006

OTHER PUBLICATIONS

S. Mallat, "A Wavelet Tour of Signal Processing", Academic Press, 2nd edition, 1999, ISBN: 0-12-466606-X.
Leif Soernmo and Pablo Laguna, "Bioelectrical Signal Processing in Cardiac and Neurological Applications",k Elsevier, ISBN: 0-12-437552-9.
Leif Sömmo and Pablo Laguna, "Bioelectrical Signal Processing in Cardiac and Neurological Applications", Elsevier, ISBN: 0-12-437552-9.

*Primary Examiner* — Scott Getzow
*Assistant Examiner* — Joseph Dietrich
(74) *Attorney, Agent, or Firm* — McGlew and Tuttle, P.C.

(57) ABSTRACT

Method for processing cardioelectric signals and corresponding device. The method enables processing previously sampled cardioelectric signals so as to filter the T wave, thereby improving the visualization of the P wave. The method comprises the following stages:

[a] dyadic decomposition the signal into bands by calculating its wavelet transform up to a range of frequencies comprised in a first range of 15 to 150 Hz and preferably 20 to 100 Hz,

[b] selection of significant bands with P wave

[c] processing of the significant bands by modifying the wavelet coefficients using statistical parametric models, and preferably statistical parametric noise suppression models,

[d] weighting the non-significant bands by multiplying them by a weighting function, and

[e] reconstructing the signal

The invention also relates to a device for carrying out this method.

20 Claims, 3 Drawing Sheets

METHOD FOR PROCESSING CARDIOELECTRIC SIGNALS AND CORRESPONDING DEVICE

FIELD OF THE INVENTION

The invention relates to a method for processing cardioelectric signals, said method being suitable for being applied to at least one cardioelectric signal from a plurality of cardioelectric signals sampled with cardioelectric signal detection means and said cardioelectric signals being obtained in the standard leads of a patient.

The invention also relates to a device comprising means for processing the cardioelectric signal, which are suitable for carrying out the method according to the invention.

STATE OF THE ART

The detection of cardioelectric signals has gained importance in recent years as a tool for studying cardiac problems.

Numerous devices are known in the art for detecting cardioelectric signals.

A first example of these devices is the surface electrocardiographs. These comprise a plurality of detectors, normally ten, that are usually arranged at various pre-established points on the surface of the human body, from which detection points the so-called standard leads are calculated, and there are twelve of said leads. The standard leads are divided into three large groups:
1. Einthoven leads, corresponding to the DI and DII leads,
2. Calculated Einthoven leads, corresponding to DIII, aVF, aVL and aVR leads, and
3. Precordial leads, corresponding to leads V1 to V6.

Each of these detectors captures a cardioelectric signal which, in fact, is the same in each case but captured at different points, which is sent to a processor that processes and represents said signal, whereby a series of data is provided which the user, in most cases a doctor, can use as a tool to make a diagnosis.

Intracavitary electrocardiographs have a sensor that is implanted in the patient's body, particularly in the heart. In the case of transesophageal electrocardiograms, this sensor is implanted in the patient's body through the oesophagus and it is advanced near the heart atrium. In both cases, applying the sensor is an invasive, very complicated and slow technique that can cause complications, some of which are serious.

Another electrocardiograph example is the so-called Holter electrocardiograph. This is a portable electrocardiograph that the patient carries during long periods of time, whereby their cardioelectric signals can be monitored continually.

Typically, a cardioelectric signal from an electrocardiograph such as those described, is a succession of wave trains, each wave train corresponding to one beat and with a first wave called P, a group of three waves called Q, R, S, more commonly known as the QRS complex, and a final wave T.

In the study of cardiac pathologies and particularly in the case of arrhythmias, the P waves, which indicate atrial activity, must be recognised immediately. Thanks to data such as the presence, morphology and duration of the P wave, it is possible to distinguish between a sinusal or ectopic P wave, or F waves that are characteristic of atrial fibrillation that is indicative of the absence of the P wave, and consequently make a more accurate diagnosis.

However, the cardiac signals from conventional, non-invasive means, such as the cardiac leads from the electrocardiographs with surface electrodes do not, in certain cases, make it possible to definitely recognise the P wave. Particularly in the case of ventricular tachycardia, extrasystoles and other arrhythmias, the P wave is usually masked by the previous T wave or the QRS complex. At present, when this occurs, for a better view of the P wave, transoesophageal electrodes or intracavitary studies have to be used. As mentioned earlier, these invasive techniques are expensive and represent a considerable risk to the patient's health.

Document WO 02/058550, published on 1 Aug. 2002, describes a system for processing cardioelectric signals which creates a train of template waves (from which the QRST section is selected), which is subsequently subtracted from a wave train that has had overlapping problems. This way, the part of the signal corresponding to the T wave of the template is removed from the signal consisting of the overlapped P and T waves, leaving the P wave without any overlapping. However, the results obtained are not always satisfactory, because the P wave cannot be neatly separated from the rest of the waves in the electrocardiographic signal and the previously selected template limits the process.

The object of this invention is to provide a method and device suitable for correctly viewing the P wave, by filtering the T wave, with both contained in a previously sampled cardioelectric signal from any device suitable for detecting said cardioelectric signals.

DISCLOSURE OF THE INVENTION

The aim of the invention is to overcome these drawbacks. This purpose is achieved by means of a method for processing cardioelectric signals from cardioelectric signal detection means, of the type indicated at the beginning, characterized in that it comprises

[a] a dyadic decomposition stage of the signal into a plurality of bands by calculating the wavelet transform of said signal using a mother wavelet, up to a range of frequencies comprised at least in a first range from 15 to 150 Hz and preferably in a first range from 20 to 100 Hz,

[b] a selection stage among said plurality of bands of at least one significant band corresponding to the frequencies of a P wave, and a plurality of non-significant bands,

[c] a processing stage of this or these significant bands, with this processing stage comprising modifying the coefficients of said bands according to a rule based on the use of statistical parametric models, and preferably applying statistical parametric noise suppression models,

[d] a weighting stage of said non-significant bands, said weighting stage comprising multiplying said non-significant bands by a weighting function, and

[e] a reconstruction stage of said signal, obtaining a reconstructed signal.

In fact, the invention proposes using the time properties of the wavelet transform, as they are more commonly known in the state of the art, to improve detection of the P wave.

The technique of obtaining the wavelet transform of a signal is described extensively, for example, in the book by S. Mallat, "A Wavelet Tour of Signal Processing", Academic Press, 2nd edition, 1999, ISBN: 0-12-466606-X, and therefore this specification does not provide any further detail on the mathematical theory associated with the transformation.

Through the wavelet transform it is possible to obtain a good representation of the signal both in time and frequency, which, for example, is not the case of the Fourier transform, which only provides information on the frequency, but not temporal information. Therefore, thanks to the wavelets, it is possible to determine the time interval when certain signal spectral components appear. In simple terms, the wavelet transform is the convolution of the signal that is to be studied, in this case the cardioelectric signal, with the wavelet function chosen for this convolution. This convolution is carried out for a set of position values in the time of the wavelet whose position and scale are varied. This way, if the wavelet in a particular position and scale is adjusted or fits in with the shape of the study signal, the value of its transform will be high; generally, it will be proportional to this adjustment.

If the cardioelectric signal is sampled or discretised, this mathematical convolution and the above-mentioned mother wavelet can be interpreted as a frequency filter, although it is not really a frequential filter, it just behaves like one. However, in the interest of simplicity, in this specification the term "filter" will be used to refer to the wavelets and frequency filter will be used to refer to the conventional frequency filter. As well as the initial calculation according to all the scales and times, only one series of decompositions corresponding to said signal is necessary, because most of the information said decompositions provide is highly redundant. For this reason, in practice, the discrete wavelet transform is used, which can provide enough information for both analysing and reconstructing a signal, with a significant reduction in the processing time by choosing a variable series of frequency bands.

So, the discrete transform uses filters obtained from the mother wavelet with different cuttoff frequencies for analysing the signal in the different scales; therefore, the signal passes through a series of highpass filters to analyse the high frequencies and lowpass filters to analyse the low frequencies.

In discrete signals, the sampling frequency is usually normalized in radians, whereby the signal sampling frequency is equivalent to $2\pi$ in terms of radial frequency. In other words, the signal's greatest frequency component will be $\pi$ radians if the sampling is done at the Nyquist frequency, which corresponds to double the maximum frequency existing in the signal. However, the frequency can be expressed in Hz in order to clarify the analysis, since in the state of the art frequency is usually expressed in terms of Hz.

Once the signal has passed through the half band lowpass filter, half of the samples can be eliminated according to the Nyquist criterion, since the signal now has a frequency higher than $\pi/2$ radians instead of $\pi$, and therefore 1 of every 2 samples will be eliminated successively until the signal is completed broken down. The preceding process is known in the context of wavelets as subband coding.

So, in practice, dyadic decomposition of the cardioelectric signal by calculating the wavelet transform, is equivalent to applying a highpass and lowpass filter to the original signal, both originating from the chosen mother wavelet. In turn, each of the signals resulting from each filter is filtered again with respective high and lowpass filters, and this way the signal is broken down successively for as many frequency bands as is desired. This way a branched decomposition of the original signal is obtained as far as the frequency band that is considered relevant, and from this a coherent set of bands is selected for reconstructing the signal.

So, for example, for a signal with a sampling frequency of 1000 Hz and bearing in mind that according to the Nyquist criterion the maximum frequency component wherein the decomposition begins must be half the sampling frequency of the initial signal, two filtered signals will be obtained: the first comprises the frequency band ranging between 0 and 250 Hz, and the second the band ranging from 250 to 500 Hz. Subsequently, the band ranging from 0 to 250 Hz is decomposed into two signals: the first comprising the frequencies ranging from 0 to 125 Hz and the second one those ranging from 125 to 250 Hz. This decomposition can be carried out successively until the more interesting frequency bands are obtained, and with the advantage that the time traceability of the signal is guaranteed, in other words, it is possible to accurately determine in which time instant a certain frequency band occurs. This applied to the temporal reading of a cardioelectric signal is equivalent to being able to determine in which time instant a P wave has occurred, in order to chose the bands that are considered more significant.

As mentioned earlier, the object of the invention is not only to be able to differentiate the P wave from the T wave, but also to try and process this signal so that the P wave can be observed particularly clearly. So, once the frequency bands that are really of interest have been detected, a processing is applied that consists in using statistical parametric models, such as for example, the Karhunen-Loeve transform, and preferably statistical parametric noise suppression models are applied. In simple terms, if we understand the original signal in X(n) in temporal terms as a sum of functions such as:

$$X(n)=Y(n)+V(n)$$

Where Y(n) is the clean signal, and V(n) is a noise coefficient that supposedly follows a statistical distribution, these models are based on the noise estimation according to the parameters of this statistical distribution, to then eliminate or reduce V(n) as much as possible in the original signal, as required. For example, the statistical parametric noise suppression models that are applicable in this processing stage include the method that uses the equivalent to the minimum mean square error criterion, also known as Stein's unbiased risk estimate. Also methods using the minimax statistical principle are applied, or a combination of the described methods. The mathematical concepts associated with these statistical models are extensively explained in the publication by Leif Sornmo and Pablo Laguna, "Bioelectrical Signal Processing in Cardiac and Neurological Applications", Elsevier, ISBN: 0-12-437552-9, and therefore no detailed explanation is provided in this description.

Through this processing stage it is possible to reduce the noise in the frequency band or bands where a better view of the P wave is required with respect to the original signal and particularly with respect to the T wave.

Before reconstructing the signal again, it is essential to minimise as much as possible the frequency bands which, containing the T wave, owing to their characteristics, temporarily overlap the frequency bands of the P wave. So, in a weighting stage the non-significant bands are multiplied by a weighting function that intends reducing their impact or simply eliminating their presence in the final reconstructed signal. This weighting function can be, for example, a constant function near to zero. However in certain cases it may be useful to use other types of functions so as not to completely eliminate some areas of the non-significant bands.

Finally, by reconstructing the electrocardiac signal it is possible to obtain a new signal wherein all those frequencies that masked the good legibility of the P event have been eliminated or attenuated, in other words those frequencies where the T wave overlapped the P wave, while the bands that contain the P wave not overlapped with T have been cleaned of noise and if necessary amplified.

In practice, it has been shown that in order to obtain a good legibility of the P event, it is advisable, and easier in computing terms, to weight the non-significant bands with constant functions, since this greatly facilitates the interpretation of the reconstructed signal. Therefore, preferably said weighting function is a constant.

The frequency components of the P wave or its harmonics are present in various frequency bands, but depending on which bands are selected, their separation with respect to the P wave may be more difficult. Therefore, preferably in said selection stage a first significant band is selected comprised in the range of 25 to 70 Hz and preferably in the range of 33 to 66 Hz. In fact, in the development of the invention, it was detected that in these frequency bands, the best compromise is achieved between the reduction of the signal by looking for harmonics in the P wave (with the consequent increase in the relative noise) and the reduction of the overlapping with the T wave. So the compromise between the maximum attenuation of the T wave and the minimum loss of amplitude of the P wave is optimum. It is worth mentioning that the QRS complex is always overlapped with the P wave and that therefore it is not possible to eliminate said complex without eliminating the P wave.

In certain cases it may be interesting to use other frequency bands where the P wave, in other words its harmonics, is separated sufficiently from the T wave, so that the T wave can be conveniently filtered. Therefore, optionally in said selection stage a second significant band is selected comprised in the range of 75 to 95 Hz and preferably in the range of 80 to 90 Hz.

Preferably said mother wavelet is a wavelet from the Daubechies wavelet family. During the development of the invention, this family of wavelets has shown a high degree of correlation with the shape of the P wave, which is precisely what we want to highlight in the cardioelectric signal. Preferably said mother wavelet from said Daubechies wavelet family is a Haar type wavelet. In fact, this grade 1 wavelet of the Daubechies wavelet family greatly resembles the shape of the signal of the P wave and particularly the shape of the P wave of the V1 lead, whereby a high degree of correlation with the original signal is achieved. This considerably improves the visibility of the P wave in the reconstructed signal.

However, other wavelets have also been found, which in certain cases are more appropriate than those from the Daubechies family. Therefore, preferably said mother wavelet is a wavelet from the Coiflet wavelet family.

As already explained, each individual case can be resolved more satisfactorily depending on the selected mother wavelet, whereby the ideal solution is to be able to select the wavelet that we want to use before the cardioelectric signal is definitively decomposed into wavelets. Therefore, preferably that prior to said dyadic decomposition stage said method comprises the following stages

[a] a stage for selecting a representative RR range from a plurality of RR ranges, detecting the T wave and the P wave.

[b] a stage for testing the mother wavelets by dyadic decomposition of at least one of said signals by calculating its wavelet transform, and

[c] a stage for selecting a mother wavelet, frequency bands and a lead or composition of optimum leads based on the minimisation of the energy of said previously detected T wave and the maximization of the energy of said P wave, for carrying out said dyadic decomposition.

An RR cycle, is the time cycle between two consecutive R events. Under the concept of representative RR cycle, the present invention considers the RR cycle during which the patient's P wave is not overlapped by the T wave, or by the QRS complex of the same RR cycle. However, it is worth mentioning that it may be that the patient does not show this P wave; in this case the method according to the invention also helps to diagnose the absence of said P wave. So, in a representative RR cycle it is possible to determine which mother wavelet best adjusts to the shape of the patient's P wave, and also which frequential subbands and leads offer a better result for each mother wavelet studied. This prior determination improves even more the results that can be obtained using the method according to the invention.

Moreover, when the cardioelectric signal detection device has several sensors, such as for example, in the case of the Holter device, several signals will be available, obtained from various leads. Each one of these leads can provide important data on the P wave, whereby it may be particularly interesting to be able to choose to which lead the method according to the invention can be applied, so as to considerably improve the results obtained.

Generally, cardioelectric signals always have a base noise originating, for example, from the actual electrocardiograph, or from the patient's muscular activity. This base noise dirties the actual cardioelectric signal and further hinders its correct reading. Furthermore, in some patients with specific illnesses, such as for example in the case of left bundle branch block, there may be some particularly difficult T waves. Therefore, optionally, prior to the dyadic decomposition a first bandpass frequential filtering is carried out ranging between 5 and 150 Hz, and preferably between 15 and 35 Hz, giving a first frequentially filtered signal. As already mentioned, at this point it is important not to confuse the filtering achieved with the wavelets, with the conventional frequency filtering, which does not provide temporal information of the signal.

Alternatively, the method according to the invention comprises a stage for a second frequential filtering using a bandpass frequential filter ranging from 25 to 45 Hz, giving a second filtered signal, said second frequential filtering being parallel to said dyadic decomposition, and in that said processing comprises a stage of non-linear combination between said second filtered signal and said reconstructed signal and a stage for attenuating the QRS wave. In fact, through this parallel frequential filtering a previously frequentially filtered signal can be obtained that already highlights frequency bands in the cardioelectric signal that are particular to the P wave. This way, thanks to the non-linear combination of both signals, it is possible to magnify even further the results obtained with the signal reconstructed from the signal processed by calculating the wavelet transform.

The method according to the invention can be applied to any type of cardioelectric signal. However, the medical community is used to interpreting cardioelectric signals from standard leads. So, preferably, said processing is carried out on the V1 lead of said detection means. This makes it considerably easier to understand the results obtained, whereby subsequently the user can make a diagnosis.

The invention also provides a device for processing cardioelectric signals, which comprises means for processing said cardioelectric signal that are suitable for carrying out a method according to the invention. So, in the many possible embodiments, for example, this device can be a tabletop electrocardiograph with an activating button for carrying out the method according to the invention and with representation means, such as a screen or a printer, which make it possible to appropriately represent the results obtained when applying the method. However, these means can also be a simple computer onto which the signals to be analysed are input, so that they can be processed and displayed if necessary.

BRIEF DESCRIPTION OF THE DRAWINGS

Other advantages and characteristics of the invention become apparent from the following description, in which, in a non-limiting manner, preferable embodiments of the invention are described, with reference to the accompanying drawings, in which.

DETAILED DESCRIPTION OF SOME EMBODIMENTS OF THE INVENTION

Figure 1:
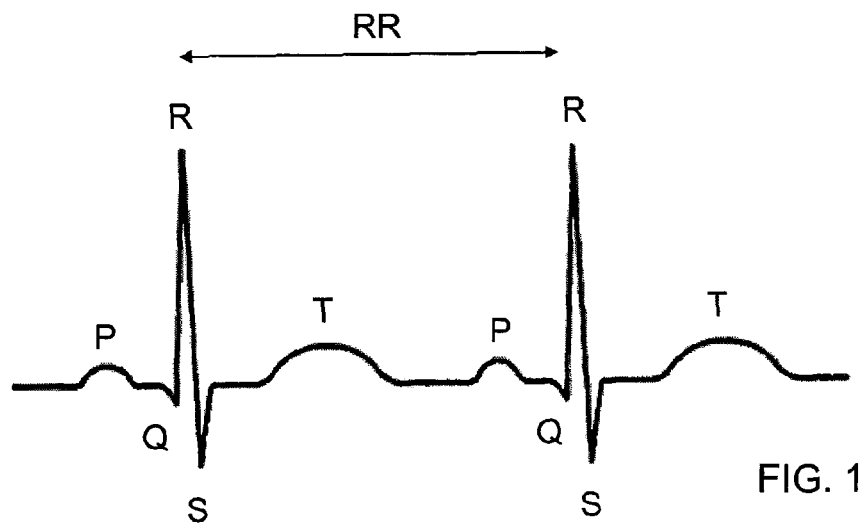
FIG. 1, a schematic representation of a cardioelectric signal with two PQRST events.

FIG. 1 shows a non-pathological RR cycle of a cardioelectric signal from standard detection means. As shown in FIG. 1, the different heart events are clearly visible, whereby in the PQRST event, there is no overlapping stage.

However, for example in the case of arrhythmias, the P wave of the signal in FIG. 1, moves and becomes confused with the T wave or with the QRS complex, whereby it is not possible to clearly distinguish it within the cardioelectric signal. When this happens, it is virtually impossible for the doctor to draw any conclusion with which to make a subsequent diagnosis.

Figure 2:
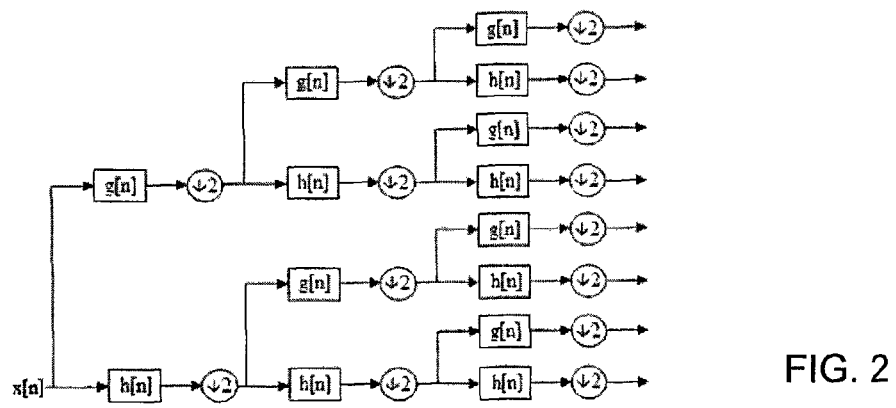
FIG. 2, a theoretical diagram of the calculation of the transform in wavelets.

So, the invention proposes a method, which makes it possible to view this P wave clearly thanks to the filtering of the T wave. In particular, one or several of the signals from the leads of an electrocardiograph, is decomposed into frequency bands during a dyadic decomposition stage, by calculating its wavelet transform. In particular, as can be seen in FIG. 2, the wavelet transform of the initially sampled cardioelectric signal $x[n]$ is calculated through convolution with a mother wavelet that is appropriate in terms of the shape of the P wave. For example, the Daubechies wavelet family, and in particular the Haar wavelet, has a high degree of correlation with the cardioelectric signal from the V1 lead of a surface electrocardiograph. Another family of wavelets with a high degree of correlation with the P wave is the Coiflet wavelet family. So, the mathematical convolution between the signal $x[n]$ and the above-mentioned mother wavelet can be interpreted as a frequential filter, although it is not a frequential filter. As can be seen in FIG. 2, the signal $x[n]$ is filtered using the lowpass mathematical filter resulting from the convolution, giving the filtered signal $h[n]$ and the actual signal $x[n]$ is filtered using the highpass mathematical filter, giving the filtered signal $g[n]$. This mathematical filtering is repeated with each filtered signal until the frequency bands considered most appropriate for carrying out the method are obtained.

Figure 3:
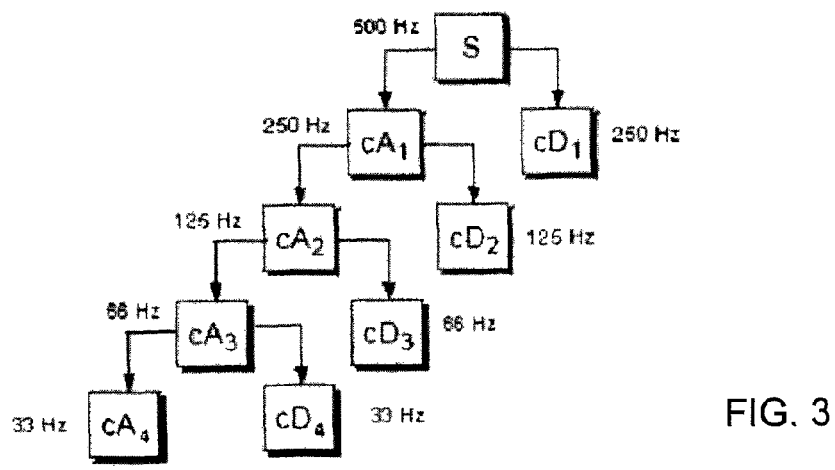
FIG. 3, a diagram of the calculation of the transform in wavelets according to the invention.

FIG. 3 shows the tree of resulting frequency bands for a signal with a sampling frequency of 1000 Hz. Taking into account that according to the Nyquist criterion the initial frequency must be half the sample frequency of the initial signal, two filtered signals would be obtained: the first comprises the frequency band ranging from 0 to 250 Hz, and the second one the band ranging from 250 to 500 Hz. Next, the band ranging from 0 to 250 Hz is decomposed into two signals: the first comprising the frequencies ranging from 0 to 125 Hz and the second one comprising the frequencies ranging from 125 to 250 Hz. In the embodiment example shown herein, this decomposition continues until the frequency bands ranging from 33 to 66 Hz are reached, which during the development of the invention have proved to be the most appropriate for applying the method because the separation of the P wave from the T wave makes it possible to filter the T wave in the optimum way.

So, according to the method, in a first stage the dyadic decomposition of the original signal is carried out as described above. Then in a stage of selecting significant and non-significant bands, those frequencies where the P wave is more clearly visible are chosen. For example, in the embodiments set out below, a particularly significant band is the one ranging from 33 to 66 Hz. The selection stage is followed by a stage for processing the significant bands, in other words the bands with the P wave sufficiently separated from the T wave. These bands are processed by applying statistical parametric models and in the examples set out below, it has been chosen to apply the one equivalent to the minimum mean square error criterion, also known as Stein's unbiased risk estimate. These models aim to suppress any disturbance in the significant band attributable to the noise of the signal. Then, the non-significant bands are weighted in a weighting stage, wherein they are multiplied by a weighting function. Normally, this weighting function aims to remove the non-significant bands which, in fact, are the ones that cause the P wave to be non-distinguishable from the T wave. Therefore, usually, the weighting function is a constant near zero. Finally, in a reconstruction stage the inverse transformation is carried out, but with the significant bands as opposed to the non-significant ones.

Optionally, prior to applying the method according to the actual invention, it could be interesting to decide which frequency bands, which leads and which mother wavelets offer the best results. Therefore, prior to the definitive dyadic decomposition a stage for selecting non-pathological RR ranges can be performed. A testing stage would be carried out in these ranges by calculating the wavelet transform of each lead with successive wavelets. Finally, in a selection stage, based on the minimisation of the energy of the T wave and the maximisation of the energy of the P wave, it would be possible to determine which bands, which wavelet and which lead is the most appropriate for carrying out the definitive dyadic decomposition explained in the preceding paragraphs.

Also, optionally with respect to the general method, it would be feasible to carry out a bandpass frequential filtering between 25 and 45 Hz parallel to the main dyadic decomposition, whereby a frequentially filtered signal would be obtained. Finally, a non-linear combination stage would be carried out between the frequentially filtered signal and the signal filtered thanks to the wavelets, in order to obtain a new signal that showed certain points, such as for example, the P waves, even more clearly.

FIGS. 4a to 4e show a plurality of 10-second cardioelectric signals from a patient with supraventricular tachycardia, which represent the same time instant. In particular, FIG. 4a corresponds to the cardioelectric signal originating directly from the V1 lead of a surface electrocardiograph. As can be seen in this figure, between 0 and approximately 7000 milliseconds, the patient shows a tachycardic event, wherein the P wave is not clearly distinguishable, in other words, it cannot be differentiated from the T wave or from the QRS complex, and therefore it is not possible to analyse the clinical signal. From 7000 ms the cardiac rhythm becomes normal again, in other words, the P and T waves are clearly differentiated because the cardiac rhythm is normal again. However, in FIG. 4b, corresponding to an intracavitary electrocardiogram, in other words where the sensors are implanted directly into the heart just to measure the P wave, it is observed that the P wave is present at all times.

Figure 4A:
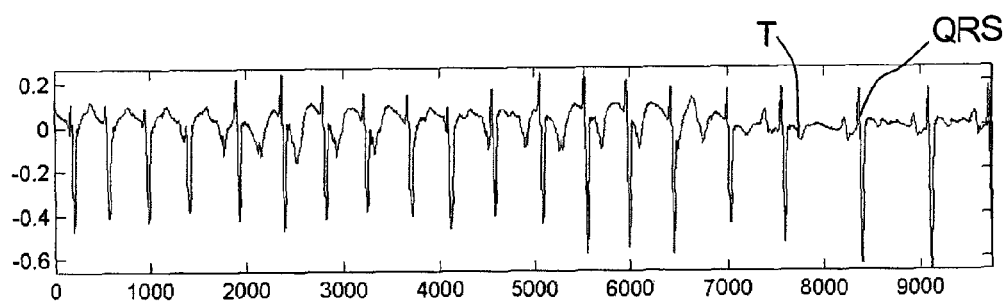
FIG. 4a, a cardioelectric signal of a patient with supraventricular tachycardia, from the V1 lead prior to the application of the method according to the invention.
Figure 4B:
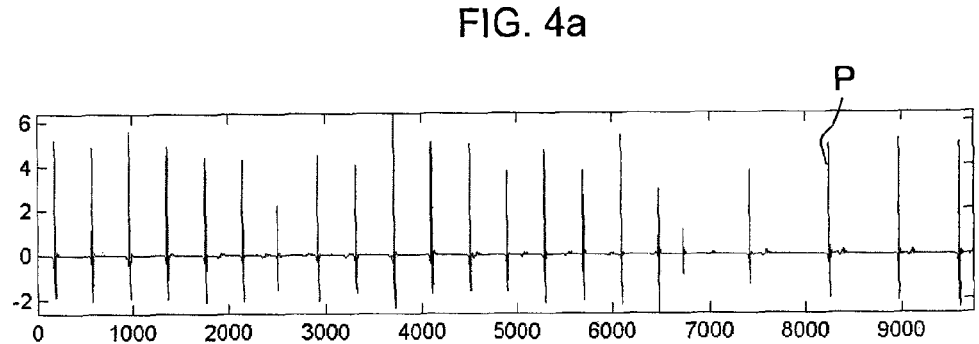
FIG. 4b, a cardioelectric signal from the same patient and from the same time instant as represented in FIG. 4a, from the intracavitary electrocardiogram for detecting the P wave.
Figure 4C:
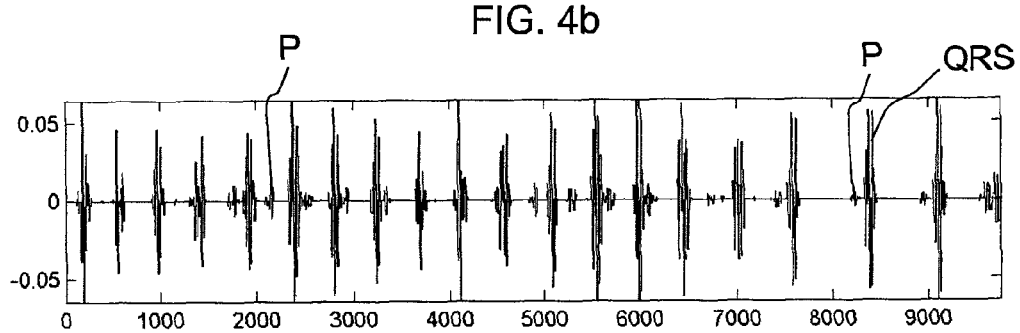
FIG. 4c, the cardioelectric signal of FIG. 4a, after applying a first embodiment of the method according to the invention.

FIG. 4c shows the result of applying a first embodiment of the method according to the invention. In particular, the applied method was first a prior filtering of the signal using a finite impulse response frequential filter, known as FIR, between 15 and 35 Hz. This filtered signal was then dyadically decomposed as far as a frequency band between 33 and 66 Hz by calculating the wavelet transform using a Haar type mother wavelet. In the significant band selection stage, the band ranging from 33 to 66 Hz was selected. In this band, the harmonic of the P wave has a relatively good amplitude with respect to the noise of the signal, but also its overlapping with respect to the T wave is very reduced. This does not occur with lower frequencies, for example from 0 to 20 Hz, where the amplitude of the P wave is greater, but due to its high degree of overlapping with the T wave, it does not allow the signal to be processed appropriately. Then, this band ranging from 33 to 66 Hz was processed using statistical parametric noise suppression models, and in particular, by modifying its wavelet coefficients with the Stein's unbiased risk estimate model. Thanks to this, the base noise was suppressed from this frequency band, thereby improving the visibility of the P wave. Subsequently, the non-significant bands, in other words, the rest of the bands, were weighted by multiplying them by the constant weighting function equivalent to zero. Finally, the signal was reconstructed following the standard reconstruction method used in the wavelets theory. FIG. 4c represents the result obtained. When compared directly with FIG. 4b, the P wave is very clearly visible, since the T wave has been filtered to such levels that make it virtually indiscernible. So in the time instants where the P wave is observed in the intracavitary electrocardiogram in FIG. 4b, it is also observed in FIG. 4c. Thus, it is clearly evident, that during the tachycardia symptoms, in other words up to 7000 ms, the P wave shifts with respect to the QRS complex and to the extent that it becomes confused with the QRS complex or with the T wave. For example at 1000 ms, the P wave is within the QRS complex. Around 7000 ms, it can be seen how the cardiac rhythm becomes normal again, in other words, the P event takes place a few milliseconds before the QRS complex and is clearly separated from the T wave. FIG. 4c shows that the T event, which in FIG. 4a is clearly separated from P, has virtually undergone complete filtering. This shows that the method according to the invention succeeds in correctly filtering the T wave and highlighting the P wave.

Figure 4D:
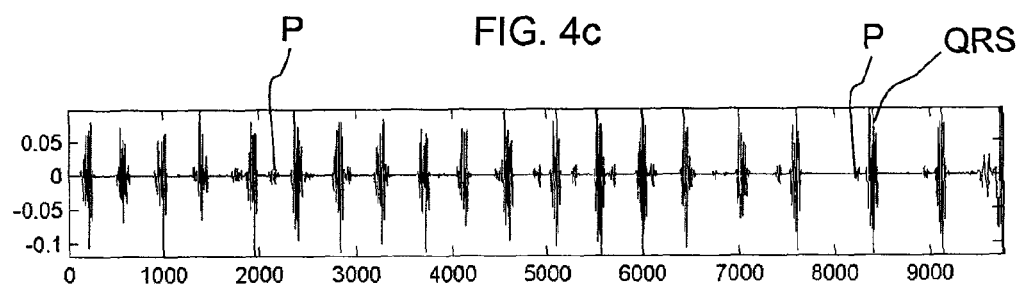
FIG. 4d, the cardioelectric signal of FIG. 4a, after applying the second embodiment of the method according to the invention.

FIG. 4d shows the application of a second embodiment of the method according to the invention with the same signal shown in FIG. 4a. In this case, the signal from V1 was frequentially filtered. Its wavelet transform was calculated directly, using a grade 2 wavelet from the Daubechies family. The chosen significant band was once again the band ranging from 33 to 66 Hz and it was also processed using the Stein criterion. The rest of the bands were multiplied by a weighting function with a value equivalent to zero. Finally the signal was newly reconstructed and the result thereof is shown in FIG. 4d. As can be seen by comparing with FIG. 4c, the information provided is very similar. This way it is possible to see how up to 7000 ms the patient has a tachycardic picture including a shift of the P wave, and from 7000 ms the patient's cardiac rhythm becomes normal again. Through comparison with FIG. 4b, it is observed that in all the points where the P event occurs, the method according to the invention detects it correctly.

Figure 4E:
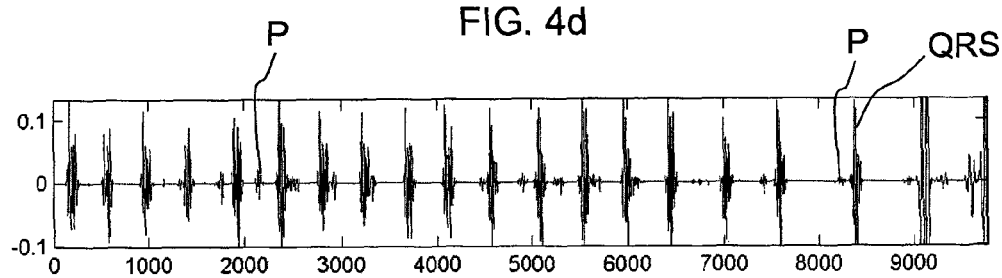
FIG. 4e, the cardioelectric signal of FIG. 4a, after applying the third embodiment of the method according to the invention.

In FIG. 4e, the signal from FIG. 4a was not frequentially filtered either. The method applied in this case was the same as that in FIG. 4d, but with the difference that the mother wavelet used was a grade 1 wavelet from the Coiflet wavelet family. As can be seen, the information that this embodiment of the method provides is similar to that provided by the embodiments in FIGS. 4c and 4d, whereby it is proved that the method succeeds in filtering the T wave and highlighting the P wave.

Figure 5A:
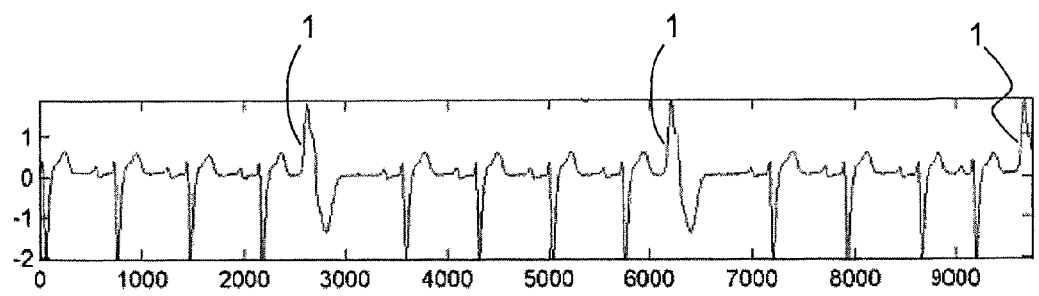
FIG. 5a, a cardioelectric signal of a patient with extrasystoles, from the V1 lead prior to applying the method according to the invention.
Figure 5B:
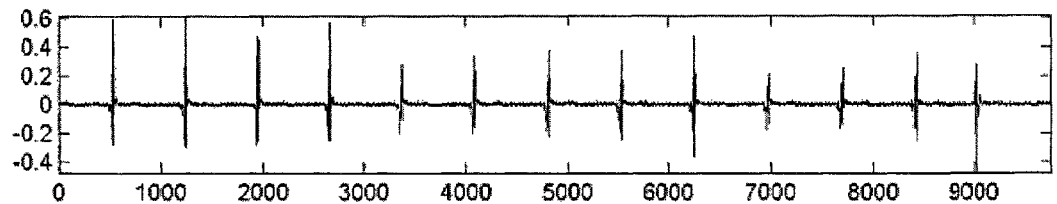
FIG. 5b, a cardioelectric signal from the same patient and from the same time instant as represented in FIG. 5a, from the intracavitary electrocardiogram for detecting the P wave.
Figure 5C:
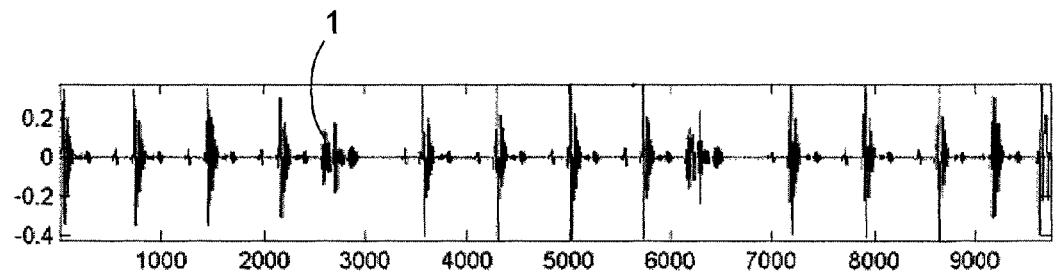
FIG. 5c, the cardioelectric signal in FIG. 5a, after applying a fourth embodiment of the method according to the invention.
Figure 5D:
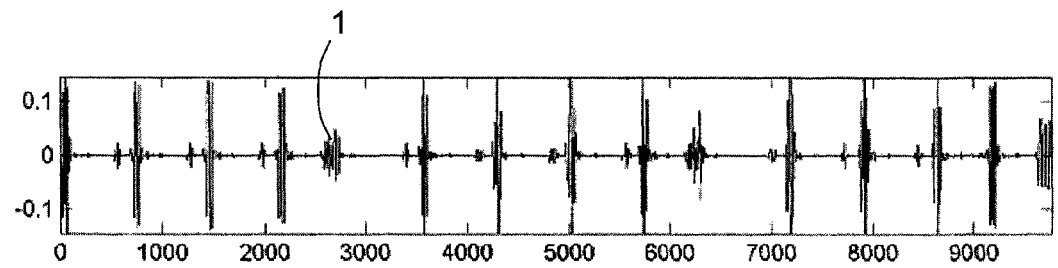
FIG. 5d, the cardioelectric signal of FIG. 5a, after applying the first embodiment of the method according to the invention.

FIGS. 5a to 5d show a plurality of 10-second cardioelectric signals from a patient with an extrasystole 1, in other words with an abnormal heartbeat, which represent the same time instant. In particular, FIG. 5a, corresponds to the V1 lead and FIG. 5b corresponds to the intracavitary electrocardiogram. In FIGS. 5c and 5d the Haar type wavelet was used for the decomposition. The selected significant band was the one ranging from 33 to 66 Hz and the remaining bands were multiplied by the weighting function that has a value equivalent to zero. These two figures differ from one another in that in FIG. 5c the frequential filter ranging from 15 to 35 Hz has not been applied, whereas in FIG. 5d it has been applied. This embodiment illustrates the case wherein frequential filtering can help to improve the method according to the invention. In this case, it is interesting to determine whether or not the extrasystoles 1 were caused by a P wave. In particular, the patient has three extrasystoles 1, the first one between 2000 and 3000 ms, the second one shortly after 6000 ms and finally the third one around 10000 ms. In the interest of simplicity, the example in the point ranging between 2000 and 3000 ms will be explained, with the conclusions being valid for the remainder of points mentioned.

In particular, with respect to FIG. 5c, wherein the frequential filter was not applied, it would appear that the start of extrasystole 1 was caused by a P wave. However, with respect to FIG. 5d, when the frequential filter ranging from 15 to 35 Hz is applied, it is observed that the P event shown in FIG. 5b, is within the QRS event and that therefore, it is not possible for the extrasystole 1 to have been caused by the P event. This proves that in certain cases prior frequential filtering can help to improve the results obtained when applying the method according to the invention.

This method was also clinically validated. The clinical study was conducted in the Electrophysiology centre of the Hospital de la Santa Creu i Sant Pau in Barcelona, Spain, with a total of 54 voluntary patients. Two simultaneous electrocardiographic tests were carried out on each patient: one surface electrocardiogram and one intracavitary electrocardiogram.

An electrocardiogram register is defined as a 10-second sequence of a V1 lead from a pathological cardioelectric signal, in other words with a P wave hidden under the T wave or under the QRS complex, which is the area where the method according to the invention is applied.

The following embodiment of the method was applied to the patient sample. The signal from the V1 lead was frequentially filtered with a 66 order Butterworth type bandpass frequential filter ranging between 15 and 35 Hz, and was then dyadically decomposed using a Haar type wavelet. The frequency band ranging from 33 to 66 Hz was selected as the significant band and the remaining bands were considered non-significant. The Stein criterion was applied to the significant band to reduce the noise and the non-significant bands were multiplied by the weighting function equivalent to zero. Finally the signal was reconstructed. This reconstructed signal was compared with the intracavitary electrocardiogram, in which the P waves were actually detected.

The following was considered to carry out the statistical study:

True positive: the P wave was detected in the reconstructed signal and in the intracavitary electrocardiogram.

True negative: the P wave was neither detected in the reconstructed signal nor in the intracavitary electrocardiogram, or the P wave in the reconstructed signal was found in the QRS event and it was detected in the intracavitary electrocardiogram. In this second true negative case, the detection of the P wave in the reconstructed signal had to be negative.

False positive: the P wave detected in the reconstructed signal did not correspond to a real P wave in the intracavitary electrocardiogram.

False negative: the P wave was not detected in the reconstructed signal, but it was detectable in the intracavitary electrocardiogram.

Two validations were made in the study: an objective automatic validation and a validation by a cardiologist.

The objective automatic validation consisted in counting the number of P events detected between the QRS event of the 10-second pathological signal. A noise threshold of the surface electrocardiogram base line was used to disregard the signals induced by noise. The number of detected P waves was compared with the number of P waves detected in the intracavitary electrocardiogram.

The validation by a cardiologist was done through a comparative interpretation study. The study was based on diagnosing the pathologies in the cases studied by first of all using the signals filtered according to the embodiment of the method previously described for this study, and secondly by using the information supplied by the intracavitary electrocardiogram as a reference.

In the objective automatic validation a statistical Chi square test was carried out on all samples. Each sample is a pathological P wave. In total, 1314 samples were obtained from the 54 patients.

|  |  | Intracavitary ECG | | |
|---|---|---|---|---|
|  |  | YES | NO | TOTAL |
| Surface ECG | YES | 361 | 95 | 456 |
|  | NO | 56 | 802 | 858 |
|  | TOTAL | 417 | 897 | 1314 |

So in the Chi squared study, the following results were obtained:

| Chi square = 725.22 | p = 0.0000 |
|---|---|
| Yates correction = 721.87 | p = 0.0000 |

Null hypothesis, H0: There is no relation between the two methods

Alternative hypothesis, H1: There is a relation association between the two methods Result: statistical significance (p=0.0000<0.05)

Therefore, in statistical terms, the method according to the invention, by filtering signals from a surface electrocardiogram, can be used to detect the P waves as an alternative to using an intracavitary electrocardiogram, as also shown in the following statistical parameters that highlight the medical significance of the test.

| Sensitivity % | 86.6% |
|---|---|
| Specificity % | 89.4% |
| Positive predictive value PPV % | 79.2% |
| Negative predictive value PNV % | 93.5% |

In the validation by a cardiologist, the "existence of P wave" variable was used, which is linked to the Positive Predictive Value (PPV). So, the total of correct forecasts in the diagnosis was 53 out of 54 patients, whereby the percentage of correct diagnosis regarding the location of the P wave was 98%.

Finally, as discussed in this specification, the method according to the invention provides data that is particularly useful for cardiology fields such as:

1. Knowing whether the P wave exists and where it is located, so that a correct diagnosis can be made out of the various types of tachycardia.
2. Detecting the presence of flutter in the case of hidden F waves.
3. Differentiating between a ventricular and supraventricular extrasystole.
4. Differentiating between tachycardia and a wide QRS complex.
5. Detecting the presence of atrial activity in the case of a hidden atrial rhythm.

Also, the method can be applied to signals from standard leads, which avoids having to fit the patient with a transoesophageal or intracavitary detector. The latter two methods increase the risk of undesired, serious effects, while the ECG, by a standard surface electrocardiogram is completely harmless for the patient. Also the transoesophageal and intracavitary detectors are not widely available in many hospital centres because of their high cost, which makes the method according to the invention particularly necessary.

The invention claimed is:

1. A method for processing cardioelectric signals, said method being suitable for being applied to at least one cardioelectric signal from a plurality of cardioelectric signals sampled with cardioelectric signal detection means and said cardioelectric signals being obtained in the standard leads of a patient, the method comprising:

dyadically decomposing said signal into a plurality of bands by calculating the wavelet transform of said signal using a mother wavelet, up to a range of frequencies comprised at least in a first range from 15 to 150 Hz;

selecting at least one significant band corresponding to the frequencies of a P wave, and a plurality of non-significant bands;

processing said at least one significant band, said processing comprising modifying the coefficients of said bands according to a rule based on the use of statistical parametric models;

weighting said non-significant bands, said weighting comprising multiplying said non-significant bands by a weighting function; and reconstructing said signal, to obtain a reconstructed signal.

2. A method for processing cardioelectric signals according to claim 1, wherein said weighting function is a constant.

3. A method for processing cardioelectric signals according to claim 2, wherein a first significant band is selected in said selection stage, said first significant band comprising a range of 25 to 70 Hz.

4. A method for processing cardioelectric signals according to claim 1, wherein said selecting comprises selecting a first significant band in the range of 25 to 70 Hz.

5. A method for processing cardioelectric signals according to claim 1, wherein said selecting comprises selecting a second significant band in the range of 75 to 95 Hz.

6. A method for processing cardioelectric signals according to claim 1, wherein said mother wavelet is a wavelet from the Daubechies wavelet family.

7. A method for processing cardioelectric signals according to claim 6, wherein said mother wavelet from said Daubechies wavelet family is a Haar type wavelet.

8. A method for processing cardioelectric signals according to claim 1, wherein said mother wavelet is a wavelet from the Coiflet wavelet family.

9. A method for processing cardioelectric signals according to claim 1, wherein prior to dyadically decomposing said signal said method comprises:

selecting a representative RR range from a plurality of RR ranges, detecting the T wave and the P wave;

testing the mother wavelets by dyadic decomposition of at least one of said signals by calculating the wavelet transform of said at least one of said signals; and selecting a mother wavelet, frequency bands and a lead or composition of optimum leads based on the minimization of the energy of said previously detected T wave and the maximization of the energy of said P wave, for dyadically decomposing said signal.

10. A method for processing cardioelectric signals according to claim 1, wherein prior to dyadically decomposing said signal, a first bandpass frequential filtering is carried out ranging between 5 and 150 Hz to provide a first frequentially filtered signal.

11. A method for processing cardioelectric signals according to claim 1, wherein said processing comprises a stage for a second frequential filtering using a bandpass frequential filter ranging from 25 to 45 Hz to provide a second filtered signal, said second frequential filtering being parallel to said dyadic decomposition, and said processing comprises a stage of non-linear combination between said second filtered signal and said reconstructed signal and a stage for attenuating the QRS wave.

12. A method for processing cardioelectric signals according to claim 1, wherein said processing is carried out on the V1 lead of said detection means.

13. A method for processing cardioelectric signals according to claim 1, wherein said first range comprises 20 to 100 Hz.

14. A method for processing cardioelectric signals according to claim 1, wherein said statistical parametric models comprise statistical parametric noise suppression models.

15. A method for processing cardioelectric signals according to claim 1, wherein said selecting comprises selecting a first significant band in the range of 33 to 66 Hz.

16. A method for processing cardioelectric signals according to claim 1, wherein said selecting comprises selecting a second significant band in the range of 80 to 90 Hz.

17. A method for processing cardioelectric signals according to claim 1, wherein prior to dyadically decomposing said signal, a first bandpass frequential filtering is carried out ranging between 15 and 35 Hz to provide a first frequentially filtered signal.

18. A device for processing cardioelectric signals comprising means for processing said cardioelectric signal, said means for processing being suitable for carrying out:

a dyadic decomposition stage of said signal into a plurality of bands by calculating the wavelet transform of said signal using a mother wavelet, up to a range of frequencies comprised at least in a first range from 15 to 150 Hz;

a selection stage among said plurality of bands of at least one significant band corresponding to the frequencies of a P wave, and a plurality of non-significant bands;

a processing stage of said at least one significant band, said processing stage comprising modifying the coefficients of said bands according to a rule based on the use of statistical parametric models;

a weighting stage of said non-significant bands, said weighting stage comprising multiplying said non-significant bands by a weighting function; and a reconstruction stage of said signal, obtaining a reconstructed signal.

19. A device in accordance with claim 18, wherein said first range comprises 20 to 100 Hz.

20. A device in accordance with claim 18, wherein said statistical parametric models comprise statistical parametric noise suppression models.

* * * * *